United States Patent [19]

Spillert et al.

[11] Patent Number: 5,783,447
[45] Date of Patent: Jul. 21, 1998

[54] HYPERCOAGULABILITY COMPARATIVE DETERMINANTS OBTAINED USING DETECTION SYSTEMS WITH VARIABLE FORCE-INDUCED ENERGY INPUTS

[75] Inventors: Charles R. Spillert, West Orange; Eric J. Lazaro, Jersey City, both of N.J.

[73] Assignee: University of Medicine and Dentistry of New Jersey, Piscataway, N.J.

[21] Appl. No.: 731,177

[22] Filed: Oct. 2, 1996

[51] Int. Cl.⁶ ................................................ G01N 33/86
[52] U.S. Cl. .................... 436/69; 436/54; 436/63; 422/61; 422/73; 600/368; 600/369; 73/64.41; 73/64.42
[58] Field of Search ................................ 436/2, 54, 63, 436/69, 70; 422/61, 73, 100; 128/637; 73/54.01, 54.02, 54.04, 54.07, 54.24, 54.27, 54.41, 64.41, 64.42; 600/368, 369

[56] References Cited

U.S. PATENT DOCUMENTS

| | | | |
|---|---|---|---|
| 3,587,295 | 6/1971 | Simons | 73/64.42 |
| 3,741,002 | 6/1973 | Simons | 73/64.53 |
| 4,026,671 | 5/1977 | Simons et al. | 422/73 |
| 4,083,363 | 4/1978 | Philpot, Jr. | 600/370 |
| 4,341,111 | 7/1982 | Husar | 73/64.42 |
| 4,705,756 | 11/1987 | Spillert et al. | 436/64 |
| 4,814,247 | 3/1989 | Spillert et al. | 436/69 |
| 4,900,679 | 2/1990 | Spillert et al. | 436/69 |
| 4,947,678 | 8/1990 | Hori et al. | 73/54.42 |
| 5,016,469 | 5/1991 | Henderson | 73/64.42 |
| 5,108,403 | 4/1992 | Stern | 606/93 |
| 5,138,872 | 8/1992 | Henderson | 73/64.41 |

OTHER PUBLICATIONS

Chandler et al. (1986) Clin. Chem. 32:505–7
Linderkamp et al. (1992) Pediatr. Res. 32:97–102
Pries et al. (1992) Am. J. Physiol. 263:H1770–8
Spillert et al. (1993) J. Natl. Med. Assoc. 65:611–6

Primary Examiner—Harold Y. Pyon
Assistant Examiner—Maureen M. Wallenhorst
Attorney, Agent, or Firm—Klauber & Jackson

[57] ABSTRACT

A method of analyzing samples of whole blood from a patient is disclosed which involves determining whether or not there is a significant difference or change in the comparative determinants of hypercoagulability in the sample. The comparative determinants are derived using two or more different detection systems, or two or more components of a single detection system, especially two or more probes, which provide variable force-induced energy inputs to the samples being measured in order to identify the presence of incipiency of a symptomatic or asymptomatic pathology caused by, or leading to, differences or changes in hypercoagulability.

76 Claims, 3 Drawing Sheets

HYPERCOAGULABILITY COMPARATIVE DETERMINANTS OBTAINED USING DETECTION SYSTEMS WITH VARIABLE FORCE-INDUCED ENERGY INPUTS

FIELD OF THE INVENTION

The present invention is in the field of methods and devices, especially diagnostic test kits, for measuring properties of hematological fluids, particularly such methods and devices used to test the coagulability of whole blood samples from mammals in order to determine the existence in said mammals of a pathological state or condition, or in order to monitor a known pathological state existing in said mammals.

1. Background of the Invention

The present invention is concerned with coagulability characteristics of whole blood, especially the interrelationships and variations of determinants of coagulability under different testing protocols, and their comparative values from one patient population to another, or in the same patient population after it has undergone a challenge to homeostasis such as disease, especially infection, or surgery. These interrelationships and variations are referred to herein as the "comparative determinants of hypercoagulability". These changing values, obtained and interpreted by the methods and devices of the present invention, become useful identifiers of existing disease states and valuable predictors of the onset of pathology.

Blood Coagulability

The coagulability of whole blood and its components has not been the object of intensive study in the medical community, despite the fact that the phenomenon of intravascular occlusion with its adverse sequelae constitutes a leading life-threatening condition in the Western world today. While alterations in the vessel wall from atherosclerosis and diabetes have been commonly incriminated in the pathogenesis of these disorders, the role of accelerated coagulation with resultant thrombus formation has received little attention because of the lack of an appropriate global screening test to prove the presence of hypercoagulability in the genesis of these and related phenomena.

There are three physiological reasons why such a test has never been developed before now. First, most coagulation tests use plasma instead of whole blood, thereby neglecting to incorporate the influence of the cellular factors in the overall coagulation process. Second, no commonly used coagulation test assesses the vital role of rapid mediator-induced endogenous cellular generation of procoagulant substances. Thirdly, no single screening test used heretofore can determine both the rate at which blood clots in a low dynamic force environment, and the potential effect on the clotting rate produced by increased input of force to the sample being tested.

The present invention addresses these problems by (1) providing a test to determine varying degrees of coagulability in a blood sample; and by (2) using a single test device with interchangeable detection systems, especially probes which make it possible to vary the energy input, i.e., force over time, to the whole blood sample, in order to quantify various whole blood sample properties and use them as differentiating criteria to assess the patient's risk of thrombosis and a subsequent ischemic event. Such detection systems able to provide variable force-induced energy inputs include, e.g., the thrombelastograph (TEG) used in its traditional configuration, along with a TEG device providing more rapid cuvette displacement; the Medtronic Hemotec ACT system used in its traditional configuration to provide higher energy input, along with the same device used with less agitation achieved by reducing the number of probe samplings of the clotting blood sample; and the International Technidyne Corporation Hemochron VI used in its traditional configuration, along with the same device in which the speed of sample rotation is increased by using larger and smaller magnets in the system. All of these detection systems are able to produce variable force-induced energy inputs to the samples being tested. However, a preferred detection system for achieving this result is the SONOCLOT® Analyzer in which different probes, as hereinafter described, are used to achieve this result. These devices and methods are described in detail further below, as are the clinical applications of the data derived therefrom for diagnostic and prognostic evaluations.

Common diagnostic tests performed on asymptomatic individuals during the course of periodic physical examinations might include a complete blood count (CBC), blood chemistries, e.g. glucose or electrolyte levels, and urinalysis, including tests for glucose, ketones, etc. Occasionally, these tests may detect a disease which was not obvious upon physical examination alone. These routine screening tests are, however, to a great extent useless in detecting at an early stage the disease states which kill and disable the great majority of individuals, including heart disease, stroke, kidney disease, cancer, inflammatory diseases, HIV infection, AIDS, peripheral vascular disease, and others. Such disease states can in part be characterized by abnormalities in either the blood coagulation or immune response system, or both.

At present, the detection in a mammal of a pathological state or condition in which the blood does not circulate freely, e.g., heart disease, cancer, AIDS, and stroke, is generally performed after the mammal has experienced some abnormal physical response, e.g. lack of strength due to diminished energy, headaches, rectal bleeding, and lumps, or as preliminarily detected during an annual physical examination. Once evidence has been uncovered of such abnormal physical responses, diagnostic procedures and/or other protocols are thereafter initiated and the results evaluated in order to identify the pathological state as well as to determine the extent of advancement of the pathological state or condition. The diagnostic procedures which are used include, among many others, X-ray analysis, e.g. mammography for breast cancer, and proctoscopy of the colon.

Additionally, once a pathological state has been found to exist in the mammal and has been qualified as to the specific pathological state, remedial procedures may be carried out in order to reduce the impact of the pathologic state on the mammal, e.g. drug treatment, radiation therapy, chemotherapy, and similar protocols, or alternately to eliminate the pathological state, e.g. by surgical procedure. In any event, the effectiveness of the remedial procedure is difficult to assess accurately on a timely basis. For example, in the surgical removal of a cancerous growth, only subsequent biopsies of proximate tissue may demonstrate that total removal has been achieved, but not with 100 percent assurance, and totally discounting the possibility of metastasis.

Tests have been developed to determine the coagulability and immune function of whole blood and its component parts, including monocytes, neutrophils, lymphocytes, etc., wherein the individual system is isolated and tested for individual functionality by diverse methods. Such procedures are costly and time consuming and are not specific to a particular pathological state. Also, the results of such tests are difficult to interpret, let alone correlate. For example, although mammography may delineate the size and location of a lump in the breast in a female, the results will not always permit a determination of whether the lump is cancerous or benign. Such pathological evaluation is carried out by observation of the actual cellular structure after biopsy or surgical removal of the lump.

Some of the above tests or procedures performed in a clinical laboratory are useful in the monitoring of certain diseases, e.g., liver enzymes for liver disease, blood urea nitrogen for kidney disease, blood urea nitrogen for kidney disease, T-cell function for immunological disorders, and prothrombin and partial thromboplastin times for bleeding disorders. However, such tests cannot determine either the effects of therapy on the coagulation changes in thrombotic diseases, or similar effects of therapy in cancer and other diseases which involve alterations in the immune defense system.

Accordingly, there has been a long felt need for a series of comprehensive methods for the determination of the coagulation behavior of blood or blood plasma which follow the temporal course of coagulation and yield data concerning the course and extent of the coagulation from which reliable conclusions regarding characteristics of the blood or blood plasma can be drawn. One process is known for example, in which the change of the consistency of blood and blood plasma is determined during the development of the fibrin net in the coagulation process. In this process a plunger is submerged in a specimen vessel, and with an oscillating up and down movement displaces the fluid whole blood or plasma specimens and thus subjects them to a flow process. The oscillating movement of the plunger is, at the same time, exceedingly small in order not to interfere with the formation of thin fibrinous threads, by a macroscopically distinct, forced flow process strongly affected by pressure. The oscillating drive of the plunger is accomplished by attaching it to the diaphragm of an acoustic transducer producing a constant frequency of 90 Hz. With increasing coagulum formation, the viscosity of the fluid specimen increases, and the resistance of the fluid to the oscillating movement of the plunger also increases in turn, so that the oscillation amplitude of the acoustic transducer diaphragm drops. This increase in resistance to the oscillation force of the plunger is measured as a change in the transmission intensity of the current through the acoustic transducer.

The main disadvantage of this known process is that only the change in resistance by the fluid specimen to the oscillation force of the plunger is measured. Accordingly, this value is dependent jointly on the change in both the viscosity and the elasticity, and is therefore tied up inseparably with these two parameters. Thus, this value cannot by itself yield any information about changes in the viscosity or the elasticity as separate parameters. A further disadvantage is that this value, which is determined by the change in the amplitude of the micro-oscillation, requires extremely sensitive measurement capability in order to detect in particular the spontaneous beginning of any change in sample consistency, since the amplitude values involved are usually minimal in the first place.

Thus, in accordance with the present invention it has been discovered that where there is a significant difference in the comparative determinants of hypercoagulability in whole blood samples of mammals as determined by using detection systems, especially probes with variable force-induced energy inputs, as detailed further below, there is a significantly increased likelihood of the presence or incipience of pathology in the patient from whom the whole blood sample was derived.

Measurements of and Clinical Applications With Respect to Hypercoagulability States Determination of the coagulation time has been most commonly used for the diagnosis of diseases such as hemophilia, von Willebrand's disease, Christmas disease, hepatic disease, and so on. Typical methods for the measurement of blood coagulation time which have been conventionally employed include those relying on the measurement of prothrombin time (PT), the measurement of activated partial thromboplastin time (APTT), the measurement of thrombin time, as well as the fibrinogen concentration. However, the subjective judgment of the operator has necessarily limited the reliability of measurements by such conventional methods, requiring that the measuring procedure be repeated to improve reliability, but often with uneven results.

The devices and methods of the present invention provide information of critical importance to the diagnosis and treatment of various pathologies, and offer a number of significant advantages over devices and methods utilized heretofore. One specific and beneficial use of the present invention is in connection with studies of blood and blood components in fields of study where the use of modern drugs that thin or thicken the blood have been hampered by the absence of means for determining the pre-existing coherence of said blood and for further determining the prospective coherence thereof after the administration of specific drugs. The present invention provides means for determining the comparative coagulation characteristics of whole blood samples or samples of blood components. With establishment of the initial and acquired coagulation characteristics, as measured by detection systems, especially probes with variable force-induced energy inputs to the whole blood samples, the medical practitioner can more efficiently determine a course of treatment and drug administration.

The devices of the present invention can provide information relating to critical characteristics of blood and other hematological fluids. The devices are intended to provide data and parameters on the coagulation of blood and other hematological fluids so that response times, mechanical properties or preferred treatment procedures may be expediently determined and regulated. Another important use of the present invention is to study blood and other hematological fluids in which the coagulation rate thereof may be indicative of deficiencies in general health, digestion, blood circulation rates, dehydration and other factors that are dependent upon the fluid circulation capabilities of the body.

2. Brief Description of the Prior Art

U.S. Pat. No. 3,587,295 to Simons discloses a test apparatus and method for providing data on the coagulation characteristics of fluids, including blood. The fluid is subjected to a mechanical energy input after which the intensity of the energy transmitted by the fluid is measured. Changes in the magnitude of applied force derived from varying amplitude of energy transmission are coordinated with the time of exposure to obtain output data that can be experimentally related to the coagulation tendencies and characteristics of the fluid.

U.S. Pat. No. 3,741,002 to Simons discloses a test apparatus similar to the one described in the '295 Simons patent, which can additionally measure the shear modulus and rheology characteristics of the fluid sample.

U.S. Pat. No. 4,341,111 to Husar discloses apparatus and methods for determining the viscoelastic characteristics of fluids which is based on an electromagnetic oscillation drive with phase shifted triggering of current flow that provides an even oscillation stimulation. The fluid specimen is acted upon by the wall of an oscillating body and responds depending on its viscoelastic properties.

U.S. Pat. No. 4,814,247 to Spillert et al. describes a method for discovering or monitoring a pathological condition in a mammal in which a cellular and chemical modulator is admixed with a cellular hematological fluid sample from said mammal, after which a reaction parameter is determined and compared to a similar parameter from a mammal of known healthy state. The reaction parameter is preferably a clotting parameter measured as fibrin levels or as a function of a time differential between fibrin levels. U.S. Pat. No. 4,900,679 to Spillert et al., contains a similar disclosure.

U.S. Pat. No. 4,947,678 to Hori et al. is concerned with a method for measuring viscosity changes in blood using a sensor comprising an endothermic or exothermic element disposed in a blood sample, after which the blood is stimulated to cause clotting and the change in viscosity is measured based on changing temperature values detected by said sensor.

U.S. Pat. No. 5,138,872 to Henderson discloses a fluid viscoelastic test apparatus comprising probe means, electromechanical transducer means, drive circuitry for providing a drive signal for generating oscillatory mechanical displacement of said probe means, response circuitry for monitoring response signals which are representative of one or more viscoelastic properties of said fluid and forming a feedback loop with the drive circuitry, circuit means for regulating an amplitude of a first signal within said feedback loop, microcontroller means for receiving and analyzing the response signals to determine the one or more viscoelastic properties of said fluid, and digital output means.

Spillert and Lazaro, "Modified Recalcification Time: A Global Coagulation Screen Test", *J. Natl. Med. Assoc.*, 65(8), 611–616 (1993), discusses a number of the principles involved in hypercoagulability.

OBJECTS OF THE INVENTION

An object of the present invention is to provide a method for identifying the existence or incipience of a pathological state in a mammal by determining whether or not there is a significant difference in the comparative determinants of hypercoagulability in whole blood samples of said mammal, derived from detection systems, especially probes with variable force-induced energy inputs to said blood samples. The changing values of these comparative determinants and their interrelationships and variations, obtained and interpreted by the methods and devices of the present invention, become useful identifiers of existing disease states and valuable predictors of the onset of pathology.

A further object of the present invention is to provide a method for obtaining comparative determinants of hypercoagulability in a whole blood sample of a mammal that may be performed in a facile and inexpensive manner and that may be effected in a relatively short period of time with minimal, if any, false readings.

Another object of the present invention is to provide a method for determining the effectiveness of a surgical procedure or other interventions on a mammal for the purpose of eradicating or preventing an existent or excipient pathological state in said mammal.

Yet another object of the present invention to provide a method for monitoring the effectiveness of a drug regime or similar protocol on a mammal having a known existent or excipient pathological state.

A still further object of the present invention is to provide a method for monitoring the effectiveness of a remedial program for retarding the growth or spread of, or reducing, eliminating or ameliorating a known existent or excipient pathological state in a mammal; and for monitoring the effectiveness of a prophylactic program for preventing the occurrence of such a pathological state in said mammal.

SUMMARY OF THE INVENTION

In accordance with the present invention there is provided a method for analyzing a whole blood sample from a mammal for determination of whether or not there is a significant difference or change in the comparative determinants of hypercoagulability in whole blood samples of said mammal, said comparative determinants being derived from detection systems, especially probes with variable force-induced energy inputs to said blood samples, in order to identify the presence or incipiency of a symptomatic or asymptomatic pathology caused by or leading to said hypercoagulability, comprising preparing anticoagulated aliquots from said whole blood sample; placing a first said aliquot in a suitable container, optionally together with a vehicle, to be used as a control aliquot; placing a second said aliquot in a suitable container, optionally together with a vehicle, to be used as an active aliquot; incubating said control aliquot and said active aliquot at from about 35° C. to about 40° C. for up to an hour or more; initiating endogenous clotting processes in the control aliquot and the active aliquot by substantially eliminating the anticoagulation thereof; measuring a blood altering process parameter and obtaining data which are comparative determinants of hypercoagulability by using two or more different detection systems or a single detection system having two or more different components, especially probes having significantly different force-induced energy inputs to the aliquots being measured; and identifying the presence or incipiency of the symptomatic or asymptomatic pathology caused by or leading to said hypercoagulability, by analysis of the comparative determinants of hypercoagulability obtained as recited above for the control and active aliquots, wherein the values for the control and active aliquots are obtained (i) at different times from the mammal, (ii) under conditions of significantly changed homeostasis of the mammal, (iii) in the absence and/or presence of, respectively, a modulator as defined herein, or (iv) from the same mammal in a healthy state, free of the pathology, and from the mammal being tested, respectively, or any combination of the above testing circumstances.

In a preferred embodiment, the method of the present invention set out above may also be carried out by substituting a different step for preparing the active aliquot, which comprises placing a second said aliquot in a suitable container together with a modulator as defined herein, and optionally together with a vehicle. The remaining steps of the method are carried out as described.

Further in accordance with the present invention there are provided methods as described above wherein the anticoagulated aliquots are prepared by mixing the whole blood with an anticoagulating agent selected from the group consisting of sodium citrate, sodium oxalate, and ethylenediamine tetraacetic acid (EDTA); wherein the modulator is present in a concentration of from about 10 µg/ml to about 50 µg/ml of anticoagulated whole blood, and the modulator is one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities, especially wherein the modulator is an endotoxin or a collagen; wherein the optional vehicle comprises a physiological saline solution; wherein the mammal is homo sapiens; wherein the incubation of the control and the active aliquot is carried out at about 37° C.; wherein preferably the incubation period will be of from about 5 minutes to about 30 minutes, more preferably from about 8 to about 20 minutes, and most preferably from about 10 minutes to about 15 minutes, but in less preferred embodiments, may be from about 1 to about 3 or 4 hours; wherein the different components of the detection system are probes, and one of the probes is substantially hollow and provides a lower force-induced energy input to the aliquots being measured, and the other probe or probes are substantially solid and provide a higher force-induced energy input to the aliquots being measured; and wherein the blood altering process is clotting.

Still further in accordance with the present invention there is provided a method as described above wherein the comparison comprises determining the thrombotic index (TI) of each aliquot at each predetermined time, the TI comprising the ratio of the recalcification time of the control ($RT_v$) to the recalcification time of the activated aliquot ($RT_i$), that is $TI=RT_v/RT_i$, using two or more different detection systems, especially probes having significantly different force-induced energy inputs to the aliquots being measured; and comparing the thrombotic index values for each predetermined time and different probe with those from each other predetermined time and different probe; and then further comparing said values with TI values for the same or substantially similar predetermined times and probes obtained by measuring whole blood samples from said same mammal in a healthy state, free of said pathology.

The particular embodiments of the methods of the present invention described above involve the addition of an anticoagulant to the whole blood sample, which is a common practice where the analytical procedures involved employ whole blood samples withdrawn from a patient some substantial time before the analytical procedures are carried out. However, the present invention also provides a method of analyzing a whole blood sample without the addition of anticoagulants thereto, comprising essentially the same above-described steps, except that the step of incubating the control aliquot and the active aliquot is carried out immediately after the whole blood sample has been withdrawn from the patient, i.e., within from about 0.1 to about 1.0 minute thereafter. The incubation time may be intentionally extended, up to about 10 minutes, and more typically up to about 5 minutes, with preferred incubation times being in the range of from about 1 minute to about 4 minutes, and more preferably from about 1.5 minutes to about 3 minutes. Also, there is no need to initiate endogenous clotting processes in the control aliquot and the active aliquot by substantially eliminating the anticoagulation thereof, since there is no anticoagulation agent present. The whole blood aliquot is simply permitted to undergo its naturally-occurring endogenous clotting processes.

There is further provided the above-described method of the present invention wherein the two or more different components of the detection system are probes having significantly different force-induced energy inputs to the aliquots being measured when used together with a suitable measuring device, and the probe with the higher force-induced energy input comprises a hollow tube of glass, ceramic, plastic or metal, the end thereof which enters the aliquot to be measured, having been sealed with bone wax or dental wax. In particular, there is provided a probe comprising a hollow tube of plastic, the end thereof which enters the aliquot to be measured, having been sealed with bone wax.

Yet further in accordance with the present invention there is provided a prepackaged diagnostic lit for use together with a suitable measuring device for analyzing a whole blood sample from a mammal for determination of whether or not there is a significant difference or change in the comparative determinants of hypercoagulability, the comparative determinants being derived using detection systems, especially probes which provide variable force-induced energy inputs to the samples being tested, in order to determine the presence or incipiency of a symptomatic or non-symptomatic pathology caused by or leading to said hypercoagulability, comprising: (1) at least one first container and at least one second container suitable for receiving aliquots of one or more samples of whole blood to serve as control and active aliquots, respectively, each optionally having a predetermined amount of a preselected anticoagulating agent therein, for preparing one or more anticoagulated aliquots of the whole blood sample to serve as control and active aliquots, for determination of blood altering process parameters thereof when used together with said suitable measuring device, each optionally containing a vehicle therefor; at least two third containers associated with means for initiating endogenous blood altering processes in the control and active aliquot by substantially eliminating the anticoagulation thereof; (2) two or more different detection systems, especially probes capable of providing significantly different force-induced energy inputs to the aliquots being measured, when used together with said suitable measuring device; and (3) a diagnostic protocol for identifying the presence or incipiency of said symptomatic or asymptomatic pathology caused by or leading to said differences or changes in hypercoagulability, comprising means for analysis of the comparative determinants of hypercoagulability obtained as recited above for the control and active aliquots, wherein the values for the control and active aliquots are obtained (i) at different times from the mammal, (ii) under conditions of significantly changed homeostasis of the mammal, (iii) in the absence and/or presence of, respectively, a modulator as defined herein, or (iv) from the same mammal in a healthy state, free of the pathology, and from the mammal being tested, respectively, or any combination of the above testing circumstances.

There is further provided the above-described prepackaged diagnostic kit of the present invention wherein the two or more different components of the detection system are probes which provide significantly different force-induced energy inputs to the aliquots being measured when used together with a suitable measuring device, and the probe which provides the higher energy input comprises a hollow tube of glass, ceramic, plastic or metal, the end thereof which enters the aliquot to be measured, having been sealed with bone wax or dental wax. In particular, there is provided a probe comprising a hollow tube of plastic, the end thereof which enters the aliquot to be measured, having been sealed with bone wax.

In a further preferred embodiment, the diagnostic kit of the present invention described above may also have present in said at least one second container for preparing the active aliquot, a predetermined amount of a preselected modulator, optionally together with a vehicle. The remaining steps of the method are carried out as described. In accordance with the present invention, there is provided the above-described prepackaged diagnostic kit further wherein said anticoagulating agent in said first and second containers is selected from the group consisting of sodium citrate, sodium oxalate, and ethylenediamine tetraacetic acid (EDTA); wherein the modulator optionally present in said second container is present in a concentration of from about 10 µg/ml to about 50 µg/ml of anticoagulated whole blood, and may be present in the second container or may be present in an a separate, additional container for dispensing to the second container; wherein a predetermined amount of the preselected modulator may also be provided as a coating on the probe to induce hypercoagulability changes in the sample being measured, and wherein the preselected modulator may also be provided in a separate container from which it may be applied to and coated on the probe; and wherein said modulator is one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities, especially wherein said immunomodulator is an endotoxin or a collagen; wherein the optional vehicle comprises a physiological saline solution which may be present in the second container or may be present in an a separate, additional container for dispensing to the second container; wherein the mammal is homo sapiens; wherein the incubation of the control and the active aliquot is carried out at about 37° C.; and wherein the blood altering process is clotting.

The prepackaged diagnostic kits of the present invention described above involve the addition of an anticoagulant to the whole blood sample, which as already mentioned is common practice. Since the present invention also provides a method of rapidly analyzing a whole blood sample without the addition of anticoagulants thereto, the anticoagulant agent may simply be eliminated from the first and second containers of the diagnostic kit; and the diagnostic protocol will indicate that the step of incubating the control aliquot and the active aliquot at from about 35° C. to about 40° C. is to be carried out for less than about 10 minutes, preferably less than about 5 minutes, and that this step is to be carried out immediately after the whole blood sample has been withdrawn from the patient, i.e., within from about 0.1 to about 1.0 minute thereafter.

There are further provided prepackaged diagnostic kits of the present invention wherein the optional vehicle comprises a physiological saline solution which may be present in the first and second containers or may be present in a separate, additional container for dispensing to the first and second containers; the diagnostic protocol indicates that incubation of the control and the active aliquots is to be carried out at about 37° C.; and there is optionally provided in the kit a heating means for obtaining and maintaining the incubation temperature.

There is still further provided improved detection systems, especially improved probes which provide variable force-induced energy inputs to samples being measured, when used together with a suitable measuring device, wherein the higher energy input probe comprises a hollow tube of glass, ceramic, plastic or metal, the end thereof which enters said sample to be measured, having been sealed with bone wax or dental wax. In particular there is provided the improved probe wherein the suitable measuring device is a SONOCLOT® Analyzer; and the probe additionally has coated thereon a predetermined amount of a preselected modulator before being introduced into said sample to be measured, wherein the modulator has previously been coated on the probe, or wherein the modulator is provided in a separate container from which it is then applied to and coated on the probe.

DETAILED DESCRIPTION OF THE INVENTION

Figure 1:
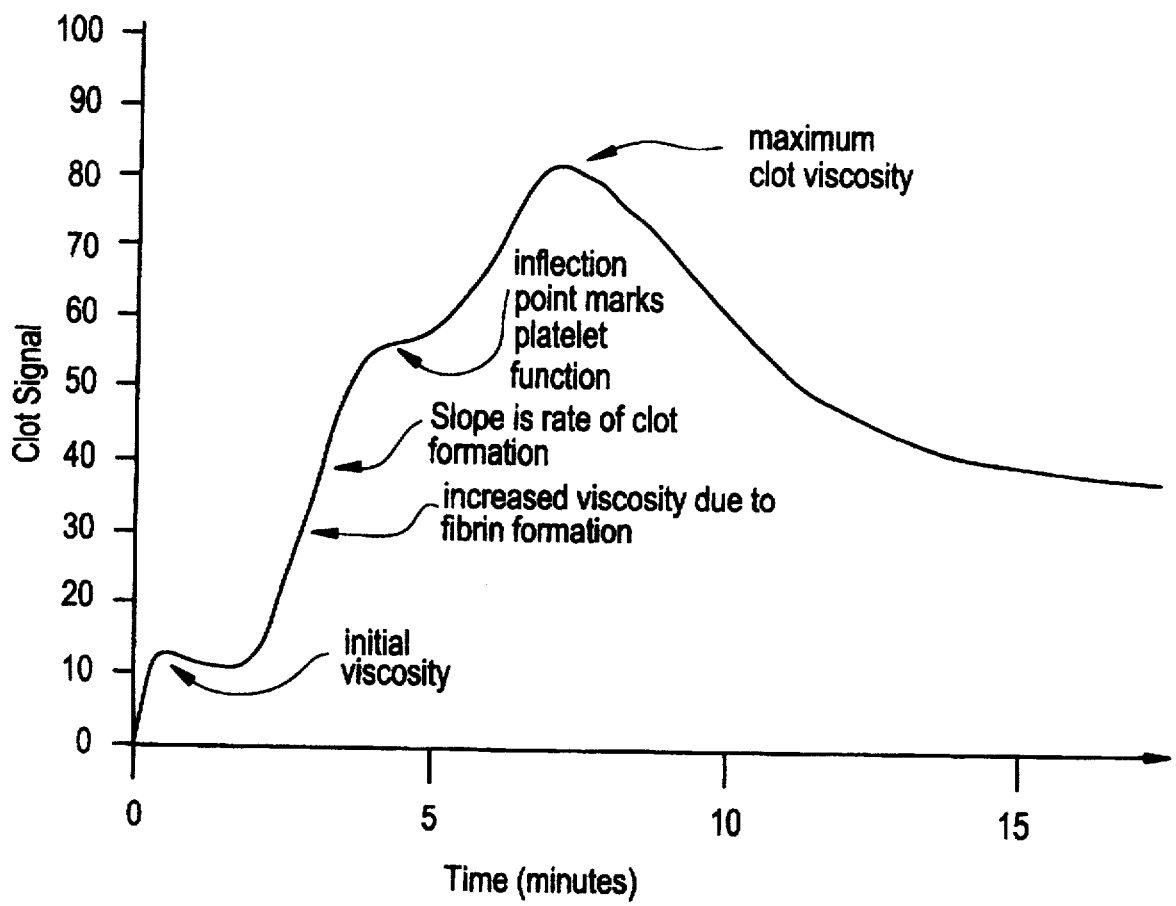
FIG. 1 depicts a graphical plot of data obtained from a SONOCLOT® Analyzer using a higher energy input probe.

One way of achieving the objects of the present invention is by determining whether or not there is a significant difference in the comparative determinants of hypercoagulability in hematological fluids from a patient, especially whole blood samples of a mammal, derived from detection systems, especially probes with variable force-induced energy inputs to said blood samples. The methods of the present invention have the advantage of being very rapid, and optionally not requiring the addition of anticoagulant agents to the whole blood sample or aliquots. Such an embodiment only requires that the apparatus necessary to carry out the test procedure be near the patient and available at the time the whole blood sample is taken from the patient for testing. The whole blood sample is allowed to undergo natural clotting in this embodiment, i.e., there is no recalcification of an anticoagulated whole blood sample, as with other embodiments of the methods of the present invention.

Hypercoagulability

In a straightforward embodiment of the present invention, the comparative determinants of hypercoagulability are obtained by using whole blood samples without any added anticoagulant or modulator. The comparative measurements are based on the readings from two or more different detection systems, especially probes which provide substantially different force-induced energy inputs to the samples being measured, when used together with a suitable measuring device, such as the SONOCLOT® Coagulation Analyzer. The final step of identifying the presence or incipiency of a symptomatic or asymptomatic pathology caused by or leading to the differences or changes in hypercoagulability measured by the probes which provide the variable energy inputs, is achieved by analysis of the comparative determinants of hypercoagulability for the control and active aliquots, wherein the values for the control and active aliquots are obtained (i) at different times from the mammal, (ii) under conditions of significantly changed homeostasis of the mammal, (iii) in the absence and/or presence of, respectively, a modulator, or (iv) from the same mammal in a healthy state, free of the pathology, and from the mammal being tested, respectively, or any combination of the above testing circumstances. However, at a minimum, these readings must be compared to those from a patient free of the incipient or existing pathology which is being investigated. At a minimum, consequently, there will be six (6) readings:

Control i) a control aliquot reading using a detection system, especially a probe with a lower force-induced energy input, ii) a control aliquot reading using a detection system, especially a probe with a higher force-induced energy input, Active iii) an active aliquot reading using a detection system, especially a probe with a lower force-induced energy input, iv) an active aliquot reading using a detection system, especially a probe with a higher force-induced energy input, Normal v) a normal aliquot reading using a detection system, especially a probe with a lower force-induced energy input, vi) a normal aliquot reading using a detection system, especially a probe with a higher force-induced energy input.

The normal values, once determined, need not usually be performed on a daily basis or be included in the routine performance of the methods and devices of the present invention. The changes, interrelationships and variations in these values comprise the comparative determinants of hypercoagulability of the present invention.

In a preferred embodiment, hypercoagulability is determined by admixing a modulator as defined herein with the cellular hematological fluid, usually a whole blood sample, of the mammal and determining a reaction parameter, also referred to herein as a "blood altering process" parameter thereof, as measured by two or more detection systems, especially probes having significantly different force-induced energy inputs and comparing the values for the reaction parameter thus obtained with values for the same reaction parameter obtained with respect to control samples, as well as comparing them to values for the same reaction parameter with respect to normal samples, i.e., with known reaction parameters of cellular hematological fluids of mammals of known healthy states, using the same or a substantially similar modulator. In a preferred embodiment of the present invention, the reaction or blood altering process parameter is a clotting parameter measured as, or determined as fibrin levels, or as a function of some given time differential between fibrin levels.

In another embodiment of the present invention, the ratio between the reaction parameters of the cellular hematological fluid of the mammal being tested, measured by two or more detection systems, especially probes with significantly different force-induced energy inputs to the samples being measured, both without and with a modulator, is compared with the ratio between the same reaction parameters of cellular hematological fluids of the same mammal of known healthy state, again measured by the same two or more detection systems, especially probes with significantly different force-induced energy inputs to the samples being measured, both without and with the same or a substantially similar modulator, to determine the existence or incipience of a pathological state in the mammal being tested.

In one embodiment of the methods of the present invention, when a hematological fluid sample, especially a whole blood sample, is taken from a mammal a substantial amount of time before the analytical procedures involved are to be performed, it is necessary to mix the sample with an anticoagulant in order to prevent clotting of the sample, which would interfere physically and otherwise with the ensuing testing procedure. For this purpose, anticoagulants for whole blood or fractions thereof include the citrates such as sodium citrate, the oxalates including sodium oxalate, sodium ethylenediamine tetra-acetic acid (EDTA), etc., with sodium citrate being generally preferred. These anticoagulant agents operate by binding to and sequestering the $Ca^{++}$ ions in the blood, which are essential components in the coagulation process.

With regard to hypercoagulability, it is known that certain reaction parameters of a cellular hematological fluid of a mammal with a pre-existing pathological condition, when admixed with a modulator as defined herein is significantly different than the same reaction parameters of a cellular hematological fluid of a mammal in known healthy state, when admixed with the same or a substantially similar modulator. Furthermore, with regard to any specific blood altering process parameter, the measurements obtained using two or more different detection systems, especially probes capable of providing significantly different force-induced energy inputs to the samples being measured, comprise the comparative determinants of hypercoagulability causing or resulting from some underlying pathology. These measurements are compared as follows:

i) active with modulator vs. active without modulator, ii) active with modulator vs. control with modulator, iii) active without modulator vs. control without modulator, iv) active with modulator vs. normal with modulator, and v) active without modulator vs normal without modulator.

The method of the present invention may not always provide a basis on which to diagnose a specific pathological condition, but it does generate evidence of the existence of a pathological condition in the mammal being evaluated.

As used herein, the term "cellular hematological fluid of a mammal" is intended to mean the whole blood thereof or a fraction thereof, including monocytes and other cellular or noncellular components of the mammal. The term "mammals" as used herein includes homo sapiens, and domesticated animals, e.g. race horses and cattle.

As used herein, the term "vehicle", with which the aliquots of hematological fluid samples, modulators, anticoagulant agents, and other components of the methods of the present invention may optionally be admixed, comprises any of those well known solvents and suspending media used by the artisan in determinations of coagulability values of test compositions. Preferably, these vehicles have a small, or at least determinable impact on the coagulability values of the test composition, and are substantially inert with respect to the test composition. However, the known ability of various solvents to alter the properties of cellular membranes, allows them to impact the coagulability of whole blood samples in particular, and as such the vehicle may effectively become a modulator as defined herein. The choice of vehicle will depend largely on the solubility characteristics of the test composition. Where the test composition is water soluble, the vehicle is preferably physiological saline. Other useful solvents, e.g., dimethyl sulfoxide (DMSO) and other well known polar and non-polar solvents, are well known to the artisan, who can select a suitable candidate for use by the application of ordinary skill and the information provided herein.

While the mechanism of action of the present invention is not fully understood, and the scope of the present invention should not be bound by any particular theory thereof, it is believed that the blood coagulation characteristics of a mammal having certain pre-existing pathological states or conditions, especially in response to a modulator as defined herein, are different from the blood coagulation characteristics of healthy mammals in response to the same or a substantially similar modulator as defined herein. Further, it is believed that the differences in these blood coagulation characteristics become even more highly contrasted and are thereby induced to yield even further information regarding pre-existing pathological states, when they are measured using detection systems, especially probes which are capable of providing variable force-induced energy levels to the samples being measured. It is also believed that the use of these different detection systems, especially probes on the same sample is capable of measuring essential characteristics of the sample relating to a blood altering process parameter such as clotting, in addition to those conventionally measured to identify a hypercoagulability state. For example, while monocytes to varying degrees are involved in the immune response system of the hematological fluid to the modulator, it is believed that the immune response system involves an interaction between the monocytes and other components, e.g., T-cells, lymphocytes, neutrophils, etc. in the cellular hematological fluid.

The pathological states and conditions, the nonspecific and even existence of which are identified by the methods and devices of the present invention include cancer; sepsis and infection; HIV infection and AIDS; diabetes; multiple sclerosis; acute myocardial infarction and other aspects of cardiovascular disease; trauma; vascular thrombosis, stroke and related pathologies; and many pathological states or conditions affecting the immune response system of a mammal. It will be appreciated by one of ordinary skill in the art that a specific pathological state or condition in a test mammal can be asserted to exist to a high degree of probability after a positive determination of such existence has been made in accordance with the methods of the present invention.

As used herein, the term "modulator" is intended to mean an agent, whether isolated in a substantially pure form, exogenously or endogenously derived, as a product of living cells on an in vivo or in vitro basis, whether naturally expressed or expressed as the product of recombinant genetic material introduced therein; or whether derived as the product of chemical or biochemical synthesis; which is the initiating or causative agent responsible for the blood altering process, especially clotting, or has a measurable impact thereon, the parameters of which are measured by the methods of the present invention.

The modulator may comprise one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities, especially wherein said modulator is an endotoxin or a collagen. In particular, it is preferred that the modulator is an immunoactivator or immunoattenuator, which is an agent that either promotes or accelerates, or retards or attenuates, respectively, coagulability or hypercoagulability of whole blood or fractions thereof, i.e. as expressed by recalcification time (RT) or modified recalcification time (MRT), as described further below. Immunomodulators also include, inter alia, endotoxins, measles and other viruses, various interferons, phorbol esters, collagens, anticoagulants such as warfarin, platelet activating factors, plasma coagulation factors or their activated forms, carrageenans, adjuvant peptides, thromboplastins, antigens, myelin, gram negative bacteria, lectins such as Concanavalin-A, and mitogens such as pokeweed mitogen.

Osterud and Bjorklid demonstrated that incubation of normal human citrated blood with endotoxin at increasing concentrations for increasing periods of time results in proportionately reduced recalcification times. Calcium ions are essential participants in the blood clotting cascade process, and can be deactivated by the addition of sodium citrate. Further addition of calcium ions, in excess of the amount which can be deactivated by the sodium citrate present, is referred to as "recalcification", and essentially reinitiates the clotting process. It has been determined that this reduction in normal recalcification time (RT), referred to as modified recalcification time (MRT), reflects hypercoagulability due to tissue factor generation and that various disease states are associated with hypercoagulability that can be related to the generation of monocyte tissue factor activity when compared with controls. The addition of a modulator, e.g., endotoxin, an activator of monocytes, to whole blood results in varying degrees of clottability directly related to the amount of tissue factor released. This activity has been further demonstrated by the fact that tissue factor antibodies totally block endotoxin-induced accelerated coagulation. Also, the degree of tissue factor activity is directly related either to transient or to persistent prior activation of the monocyte in vivo. Therefore, the distinguishing feature of the test is based on the variation in tissue factor production, which depends in turn on the duration and intensity of these stimuli. In a preferred embodiment of the present invention, the effect of tissue factor on coagulability can be quantitated by measuring the MRT with numerical precision using an instrument, the SONOCLOT® Coagulation Analyzer (Sienco Inc. Morrison, Colo.), that can detect the early stages of clot formation, i.e., the incipient clotting process cascade, and is similar in performance to the thrombelastograph.

The term "hypercoagulability", as used herein denotes a coagulation state of enhanced clottability established by the persistent shortening of the clotting time of blood as determined by the MRT or any other suitable test. The finding of such hypercoagulability strongly suggests the risk of developing thrombotic vaso-occlusive pathologic processes affecting the major arterial and venous circulations.

As already discussed, there exists a difference between the blood altering process reaction parameters of cellular hematological fluids of healthy mammals to a modulator as defined herein, especially an immunomodulator, compared to reaction parameters of cellular hematological fluids of a mammal having a pre-existing pathological condition responsive to such a modulator, especially an immunomodulator. Thus, where the context of the blood altering process is clotting parameters, and specifically recalcification times, a comparison thereof readily identifies a mammal having an existing pathological condition. Many algorithms may be developed using such blood altering process reaction parameters, and more specific algorithms may be derived to more fully evaluate particularly clotting parameters to determine the existence in a mammal of a specific pathological condition or state.

A more sophisticated algorithm is based upon the calculation of a "Thrombotic Index", defined as a ratio of the recalcification time ($RT_v$) of the cellular hematological fluid of a mammal (in a vehicle, e.g. saline) in the absence of an immunomodulator, to the recalcification time ($RT_i$) thereof also in a vehicle and in the presence of an immunomodulator, in accordance with the following equation (I):

$$TI = RT_v \div RT_i \qquad (I)$$

with the thrombotic index of the mammal being tested being compared with the thrombotic indices of healthy mammals. Still another algorithm is formulated by a percent difference of clotting (PDOC) in accordance with the following equation (II):

$$PDOC = \frac{RT_v - RT_i}{RT_v} \times 100$$

The percent differences of clotting of test mammals are then compared with percent differences of clotting of healthy mammals.

There are many devices available for measuring reaction parameters, e.g. chromatographic columns for concentrations of a specific chemical, as well as for measuring clotting parameters. For example, a SONOCLOT® Coagulation Analyzer is available from Sienco, Inc. for measuring viscoelastic properties as a function of mechanical impedance of the sample being tested. Such analysis is very sensitive to fibrin formation, thereby providing improved sensitivity and reproducibility of results. Other detection systems able to provide variable force-induced energy inputs include, e.g., the thrombelastograph (TEG) used in its traditional configuration, along with a TEG device providing more rapid cuvette displacement; the Medtronic Hemotec ACT system used in its traditional configuration to provide higher energy input, along with the same device used with less agitation achieved by reducing the number of probe samplings of the clotting blood sample; and the International Technidyne Corporation Hemochron VI used in its traditional configuration, along with the same device in which the speed of sample rotation is increased by using larger and smaller magnets in the system. All of these detection systems are able to produce variable force-induced energy inputs to the samples being tested. However, the preferred detection system for achieving this result is the SONOCLOT® Analyzer in which different probes, as hereinafter described, are used to achieve this result.

In order to facilitate a better understanding of the present invention, the following description relates to the known procedure for measuring "modified recalcification time" (MRT), particularly with reference to the use of a specific endotoxin, E. coli endotoxin (strain 055:B5) as the immunomodulator in a suitable vehicle, e.g. saline, in studying its impact on the recalcification time-endotoxin ($RT_i$). For the most part, the MRT procedures are the same as those employed in the methods of the present invention, except for the critical distinction with respect to the use of detection systems, especially probes which provide for variable force-induced energy level inputs to the samples being measured, which in turn allows for very short incubation times, as well as the omission of the anticoagulation step, which also avoids the need for recalcification.

As indicated, in the MRT procedure, a fairly lengthy incubation time is required, sometimes as long as four hours, in contrast to the very short incubation time required with the methods of the present invention, of up to one hour. Often, the reactions talking place in the whole blood sample from which the comparative determinants of hypercoagulability are measured, may be virtually instantaneous, requiring only a few seconds at most. Indeed, in one preferred embodiment, a whole blood sample which is withdrawn from a patient is not treated with an anticoagulating agent, but is dispensed directly to a cuvette for the suitable measuring device, where the cuvette is maintained at about 37° C. and is installed in the suitable measuring device and measurements are taken without intentional delay. In this embodiment, consequently, the incubation period is very brief, and may occupy a mere matter of seconds, up to about one minute or so. It is noted in this context that human blood will normally clot at room temperature and when exposed to air under normal conditions, in a matter of from about 4 to 8 minutes, more typically in about 6 minutes. Thus, where no anticoagulating agent is used, it will be necessary to dispense the whole blood sample to the cuvette and carry out the desired measurements within the context of that clotting time frame.

In other embodiments, where no anticoagulating agent is used, but an intentional incubation period of some predetermined duration is carried out, the reactions will be sufficiently complete to permit accurate measurements within a few minutes, typically up to about 10 minutes, and more typically up to about 5 minutes, with preferred incubation times being in the range of from about 1 minute to about 4 minutes, and more preferably from about 1.5 minutes to about 3 minutes.

It should be pointed out that in other embodiments of the present invention, where the whole blood sample is treated with an anticoagulating agent and longer incubation periods are used, that these incubation periods will preferably be of up to about 1 hour in duration. Preferably, the incubation period will be of from about 5 minutes to about 30 minutes, more preferably from about 8 to about 20 minutes, and most preferably from about 10 minutes to about 15 minutes. In other, less preferred embodiments of the present invention, the incubation periods may be even longer, such as from about 1 to about 3 or 4 hours. Such extended incubation periods remain within the scope of the present invention, but they not only require that the whole blood sample be treated with an anticoagulating agent, but are contemplated to be more nearly like the known below-described modified recalcification procedure, and thus less likely to reveal the desired comparative determinants of hypercoagulability obtainable with the methods and devices of the present invention.

Modified Recalcification Time Procedures

In the evaluations described further below, the following test protocol was followed. From a mammal to be tested, there is withdrawn a hematological sample, e.g., by venipuncture using a syringe (20 gauge needle) without stasis or undue force to draw blood. It will be appreciated by the artisan from the discussion herein that traumatization during blood sampling should be kept to a bare minimum, since imperfect sampling introduces tissue factors into the blood sample and thus will have an adverse impact on the validity of the results. The hematological fluid is transferred to a tube usually including, but in any event is admixed with an anticoagulant, e.g., a 3.8% solution of buffered sodium citrate. Generally, the volumetric ratio is about nine (9) parts hematological fluid to about one (1) part anticoagulant. While many anticoagulants are available, sodium citrate is generally preferred since the pH level thereof is essentially similar to the pH level of the hematological fluid of the mammal being tested, and is less toxic to the cellular elements.

Thereafter, an aliquot portion (about 2 milliliters) of the anticoagulated hematological fluid or citrated whole blood (CWB) is admixed in a tube with the endotoxin (e.g. 20 µL of a 1 mg/cc suspension or solution of $E.\ coli$ endotoxin) and incubated for a predetermined time period, generally of from about 2 to about 4 hours. It has been generally found that longer incubation time periods provide results of greater sensitivity.

Generally, incubation temperatures range from about 35° C. to about 40° C., preferably about 37° C. After incubation, a predetermined amount of a calcium-ion containing composition, such as calcium chloride ($CaCl_2$), e.g., 10 µL of 0.5M $CaCl_2$ is admixed with 0.4 cc of the incubated hematological fluid with the admixture introduced into a cuvette for insertion into the above-mentioned SONO-CLOT® Coagulation Analyzer, set to determine a recalcification time between initial fibrin formation and a "given" fibrin concentration, e.g. a 10% scale deflection is taken as an end point. It is understood by one skilled in the art that calcium ions are necessary to initiate fibrin formation.

For recalcification times based on an immunomodulator ($RT_i$) with mammals in a healthy state, a cellular hematological fluid for such mammals in a healthy state will range between 4.6 to 7.2 with a mean of 5.69, as determined by SONOCLOT® Coagulation Analyzer.

For recalcification times based on an immunomodulator ($RT_i$) with mammals having a pathological condition, a cellular hematological fluid for such a mammal having a pathological condition, as subsequently confirmed by other diagnostic procedures, will range above or below the $RT_i$ values of healthy mammals, as more fully hereinafter disclosed and discussed.

Statistical analysis is used to assess and summarize data in order to make such data comprehensible and to be able to draw appropriate conclusions from the results. Discussion of the following Examples includes certain statistical analyses that will permit a better understanding of the present invention. As used herein, the term "statistically significant differences between the groups studied" means that when using the appropriate statistical analysis (e.g. t-test) the probability of the groups being the same is less than 5%, e.g., $p<:0.5$. In other words, the probability of obtaining the same results on a completely random basis is less than 5 out of 100 attempts.

Devices for Determining Hypercoagulability

A number of different devices may be used to perform the measurements necessary to carry out the methods of the present invention. For example, a fluid viscoelastic test instrument constructed in accordance with the present invention may have a hinged head assembly containing a transducer. The transducer may simply comprise an off-the-shelf electromechanical audio speaker having a suitable impedance. A disposable probe may be removably attached to the transducer, and a disposable cuvette, adapted for holding a fluid sample, is received by a cuvette holder. When the head assembly is in a lowered position, the probe is brought into contact with the fluid sample contained within the cuvette. A ready indicator, which may comprise a light emitting diode (LED), indicates that a platen has heated the sample to the desired temperature of 37° C. A heating indicator, which may also comprise an LED, indicates that the temperature of the platen is below the desired temperature. A MIX/ZERO switch comprises a double pole double throw switch adapted for momentary closure in both directions. One pole generates two logic level inputs, MIX and ZERO, monitored by a microcontroller. The other pole uses only the MIX position of the MIX/ZERO switch to activate a mixing motor for ten seconds when the switch is moved to the MIX position. A liquid crystal display (LCD) is employed to report analysis results and operator prompts.

A particular utility for the fluid viscoelastic test instrument with the present invention lies in detecting physical characteristics of a blood sample, generating the time varying graph or signature of a blood sample during the period of time over which coagulation of the blood occurs, and analyzing that signature to extract data that quantifies variables of coagulation performance. Different detection systems, especially probes capable of providing significantly different force-induced energy levels to the samples being measured are used for generating the coagulation signature of a given sample. A typical coagulation signature begins with the instrument prepared to accept a blood sample. A disposable probe of a preselected type is attached to the transducer. A disposable cuvette having a mixing bar is mounted within the cuvette holder. A blood sample, which may either be anitcoagulated or have no anticoagulant agent added, is added to the cuvette containing calcium chloride, $CaCl_2$, to neutralize the citrate, and the MIX/ZERO switch is momentarily moved to the MIX position. A mixing motor, magnetically coupled to the mixing bar, is operated for stirring the blood sample contained in the cuvette for a preferred time period of ten seconds. After stirring has stopped, the head assembly is manually lowered, thereby inserting the probe into the cuvette. The instrument remains in this configuration during analysis of the blood sample. An analog output voltage signal is typically coupled to a conventional external strip chart recorder. Automated analysis of the blood sample is performed by a microcontroller, which reports results on a display. Following analysis of a blood sample, the head assembly is raised and the disposable cuvette containing the blood sample and the disposable probe are both discarded.

A typical graphical output signal or signature, such as would be recorded on an external strip chart recorder over the period of time during which coagulation of a blood sample would occur, will exhibit a vertical displacement that corresponds to the analog output voltage signal. The greater the displacement produced by the signal, the greater the value of an oscillator gain voltage signal. Horizontal displacement in the graph corresponds to time, typically scaled to 0.5 cm per minute.

Probes with Variable Force-Induced Energy Inputs

The particular construction of the probe, which is preferably disposable, used in the devices of the present invention as described above is a critical aspect of the present invention. In a representative construction, the lower portion of the probe carrier is formed of a resilient material and is provided with a counterbore adapted to receive an end of an exciter rod, which is the probe itself. The exciter rod probe is of a fixed length, and accordingly, when it is introduced into the counterbore, it will extend a prescribed distance downwardly therefrom so that the free end thereof is engaged within the sample cup. With a 0.4 cc sample in the cup, the free end of the probe will be immersed in the sample. When the driving device is powered, the essentially non-elastic exciter rod-probe will be moved longitudinally in a vibrational mode to mechanically agitate the sample in the cup.

When used to generate a lower energy input coagulation data signature of the blood sample, the exciter rod-probe is hollow in conformation, which also facilitates accommodating and securing it in the counterbore of the probe holder. However, it has been discovered that this design feature, while perfectly adequate for measuring the desired low energy input coagulation parameters in a blood sample, is not capable of measuring or determining the high energy input coagulation data signature of the same blood sample. By generating both the lower and higher energy input coagulation data signatures, hypercoagulability consistent with a significantly increased likelihood of a present or incipient pathology, can be much more successfully pinpointed.

Heretofore, coagulation tests which have been performed with instrumentation designed to provide clot detection, have been characterized by the application of a constant level of force-induced energy input to the sample of clotting blood throughout the determination of clotting time. A key feature of the present invention, which represents a significant departure from current procedures, is the application of varied force-induced energy level inputs to the blood samples undergoing clotting. For example, two aliquots of the same blood sample are permitted to clot with the application of two different force-induced energy level inputs delivered by two different detection systems, especially probes, either forming a part of two different instruments or being used sequentially in the same instrument; and the coagulation profiles of each aliquot are determined and compared to that of the other, as well as to those of the control samples and normal samples.

The application of varied force-induced energy level inputs to blood samples undergoing clotting is achieved with the variable force-induced energy input detection systems, especially probes of the present invention. These tubular probes oscillate within the blood sample. The associated instrument detection circuitry senses the resistance to motion that the probe encounters as the blood sample progresses through the fluid, fibrin formation, and then clot dissolution stages. The data that is generated is then recorded on a printout in which the clot signal, i.e., the relative impedance, is plotted as the ordinate on the y-axis against time as the abscissa on the x-axis. Generally, a major portion of the time required for blood coagulation is the period elapsing before formation of activated thromboplastin in the blood, since the reaction proceeds slowly. Thereafter, transformation from fibrinogen to fibrin occurs rapidly, whereupon the blood loses its fluidity and becomes coagulated. During these stages of blood coagulation, the viscosity of the blood is also changing, and measurement of these changing values, on either an intermittent or a continuous basis, permits determination of the so-called kinematic viscosity of the blood.

In order to generate a higher force-induced energy input into the blood sample from the probe in accordance with the present invention, the standard disposable hollow probe described above is used in determining the lower force-induced energy input level to the particular and comparative samples involved, while a modified probe is used to provide a higher force-induced energy level input to the same particular and comparative blood samples. The probe may be modified in a number of different ways so long as it still provide a suitable increase in the force-induced energy input into the blood sample in accordance with the present invention. One modification that has provided satisfactory results has been to seal the end of a hollow probe which enters the blood sample with a relatively hydrophobic material that is sufficiently pliable to be introduced into the end of the hollow probe to a depth of about 0.5 cm, where it becomes permanently lodged. The material may have an elastic, pliable character that does not change; or it may be flexible at first, and then harden into a concrete mass in the hollow probe. Suitable materials of this type include bone wax, available from ETHICON®, and dental wax. Bone wax can be used to fill the opening of the hollow probe at room temperature, while dental wax is preferably first melted and then cooled to room temperature before being used to fill the opening of the hollow probe. In addition, bone wax has been proven to promote coagulation of whole blood, and thus has the added utility of being able to promote or accelerate a blood altering process of interest while at the same time measuring the response of the whole blood sample thereto.

The hollow probe can be made of non-reactive metals such as aluminum, bronze or stainless steel, or of various glass, ceramic, or synthetic resin compositions well known to the artisan who fabricates diagnostic equipment for medical use. It is desirable that these materials be as inert as possible, in order to avoid unwanted reactions with and of the constituent parts of the blood sample. The varying density of these materials will have a slight, but calculatable effect on the force-induced energy which they impart to the blood sample. The hollow probe imparts less force-induced energy to the blood sample than a filled hollow probe or solid probe precisely because it is hollow, so that only the thickness of the end portion of the cylinder comprising the hollow probe actually contacts the blood sample. The column of only slightly compressible air trapped in the end of the hollow probe is also capable of imparting force-induced energy to the blood sample, but this will still be substantially less than the force-induced energy which is imparted by a filled hollow probe or a solid probe.

As indicated, a solid probe, i.e., one made of a single material without any cavities, is also suitable for use in the present invention. The materials from which such solid probes may be fabricated are the same materials as were described above for construction of suitable hollow probes. The density and elasticity of the material which is chosen for fabricating the solid probe will be largely determinative of any variation in the force-induced energy input level to the blood sample, assuming that the same oscillating force is applied to the probe by the instrument in all cases. This assumes, however, that the geometry of the solid probe is that of a simple cylinder, the end plane of which is perpendicular to its main axis. Other geometries are useful, and will also provide variable force-induced energy input levels, as is the case with the hollow probe and the filled probe. For example, a truncated cylinder may be chosen as the spatial form for the probe, or it may be pointed, i.e., a sharp, narrowly rounded tip. The probe does not have to be cylindrical in form, having a circular cross section, but may have an elliptical cross section, or may be a rectilinear solid having a square, octagonal or other cross section. The surface characteristics of the probe may also be varied as well. The surface may be smooth or have varying degrees of roughness. The surface may also be provided with projections of various types and sizes, e.g., pointed or threaded projections, fins and baffles. The surface of the probe may also be coated or impregnated with one or more of the various materials comprising the modulators as defined herein, e.g., antigens, antibodies, immune cells, and platelet or other blood cell coagulation activators or inhibitors which promote or inhibit changes in the blood sample with regard to hypercoagulability.

It is theorized that the solid exciter-rod probe displaces more of the fluid sample with every stroke of its longitudinal vibration than would be the case where the exciter-rod probe has a hollow configuration, and is as a consequence able to impart a greater amount of force-induced energy to the fluid sample. With a greater amount of force-induced energy input comes a correspondingly greater force-induced energy output, and thus a higher degree of sensitivity from the same sensing means. It is preferred to use the SONOCLOT® Analyzer, since the lower and higher force-induced energy inputs and corresponding hypercoagulability measurements can be carried out with the same device, by simply using different exciter-rod probes for each measurement. However, it is also within the scope of the present invention to employ other devices which are capable of providing the same coagulation signature analysis and measurements as are required for the present invention, preferably using a single instrument.

Clotting Assay Using Probes with Variable Force-Induced Energy Inputs

In a typical assay, 1.0 ml of citrated whole blood is brought up to 37° C., after which the sample is gently mixed and 300 µl aliquot samples are pipetted into the cuvettes of the instrument containing a small magnetic stirrer and 40 µl of 0.1M calcium chloride, $CaCl_2$. The calcium chloride neutralizes the excess citrate anticoagulant and the sample will begin to clot. One SONOCLOT® Analyzer or other instrument will contain a hollow probe, while the other(s) contain a solid probe or a hollow probe filled with bone wax or other suitable material. The samples are mixed and the clotting profiles of both samples are obtained.

The clotting time, which is automatically displayed on the instrument chart, is significantly reduced in the filled probe sample when compared to the standard, hollow probe. The filled probe sample is the one with the greatest energy input because when vibrating axially, it displaces the most fluid. The traditional hollow plastic SONOCLOT® Analyzer probe produces a 1.3 $mm^2$ horizontal surface area in contact with the blood sample. The wax filled or solid probe has a 50.3 $mm^2$ area, which represents a 38.7 fold increase in area of probe able to input energy to the blood sample. Thus, the same sample aliquots analyzed on two instruments with either a solid or hollow probe can generate useful clinical information on apparent viscosities and thereby become an important adjuvant in diagnostic decision making.

It is possible to extend the useful range of testing in accordance with the present invention by utilizing two or more instruments with different probes simultaneously. For example, when the SONOCLOT® Analyzer is used to measure recalcification times, the amplitude of the curve rises above the baseline values for the blood sample as the cellular and other biochemical components of the clotting blood generate fibrin. Fibrin monomers are formed when fibrinogen is cleaved to form fibrinopeptides, which associate together to form a polymeric material, fibrin, sometimes referred to as the fibrin net, which increases the viscosity of the blood as more and more fibrin is produced. The measurement process of the present invention monitors the liquid blood from a point before fibrin formation begins up to the point where a solid mass of fibrin forms a clot, which is the endpoint of the clotting process. Characteristic portions of the clotting signal, which are readily identified from a graphic plot of the data, represent critical aspects of the platelet function, a key portion of the clotting process.

FIG. 1 is a typical graphic plot of relative impedance (clot signal as a %) on the y-axis versus time (in minutes) on the x-axis. The curve produced by the data points obtained from the impedance analysis of a blood sample yields important information in a number of regards. The plateau at the lowest clot signal value is indicative of the initial impedance of the blood sample, before any noticeable clotting has taken place. The steepness of the slope over the next portion of the curve is indicative of the rate of clot formation resulting from fibrin formation. The next area of the curve of significance is the observed inflection point, which is a marker of platelet functioning in the blood sample. The inflection point defines the relative impedance at a particular time of formation after recalcification, i.e., initiation of coagulation. The next point on the curve is the maximum clot impedance. This value, together with the time required to reach this value, are also important criteria in establishing a useful coagulation profile for the blood sample.

Utilizing the variable force-induced energy input detection systems, especially probes of the present invention, it is possible to alter these values, i.e., obtain different readings for the initial impedance, slope, inflection point, and maximum impedance from the same blood sample. These values, when determined for a normal population in a study, provide a benchmark or baseline to which the values from patients in the same study can then be compared. The values obtained with the higher force-induced energy input probe, which provides increased sensitivity, establish enhanced or newly visible markers of existing or incipient pathology in the patients providing the blood samples, especially when viewed in the context of the values obtained with the lower force-induced energy input probe, which detects hypercoagulability in the same blood sample in accordance with known procedures at approximately the same time after initiation of clotting.

Clinical Evaluations Based on Variable Force-Induced Energy Input Data

Further, it has been discovered that there is a significant reduction in clotting times when the higher force-induced energy input probe, i.e., the filled hollow probe or solid probe, is used instead of the customary hollow probe in hypercoagulability determinations. It is theorized that this result may be due to the greater amount of energy being imparted to the blood sample, which may stimulate or directly activate an increased production of clotting factors, leading to more rapid fibrin formation. It may also be responsible for inhibiting anticoagulant activity or factors in the blood sample. Where the higher force-induced energy input probe is a hollow probe sealed with bone wax, the bone wax itself may be responsible for a portion of the reduction in clotting time, since bone wax has been shown to accelerate platelet function and may accentuate platelet initiated clot formation.

It has also been found that in approximately ten percent (10%) of blood samples evaluated, that the clotting time observed with the higher force-induced energy input probe is actually prolonged, rather than reduced, when compared to the results observed with a lower force-induced energy input probe. It is theorized that in these cases the increased force-induced energy imparted to the blood sample may delay the association and binding together of fibrin monomers to a sufficient extent to establish a functional fibrin net capable of producing significant clotting. It is also possible that these results are caused by, or are indicative of inadequate platelet functioning in the blood sample wherein platelet aggregation is insufficient to form a clot. The increased force-induced energy level may prevent platelet aggregation, or platelet adhesion to fibrin or other cells, or may even produce detrimental changes in the fibrin macrostructure itself.

Especially significant comparative data have been obtained from a study of preoperative and postoperative coagulation profiles in patients, using the variable force-induced energy input detection systems, especially probes of the present invention. In this study aliquots of citrated whole blood obtained just prior to surgery were compared to whole blood samples obtained after surgery. The samples were placed in an incubator for ten minutes until they reached 37° C., after which they were placed in SONOCLOT® Analyzer cuvettes, also at 37° C., containing 40 µl of 0.1M calcium chloride. The samples were mixed and the recalcification times determined. The data obtained are shown in the table below:

| Mean Recalification Time (Sec ± SD) | | | |
|---|---|---|---|
| Preoperative Lower Energy Probe | Preoperative Higher Energy Probe | Postoperative Lower Energy Probe | Postoperative Higher Energy Probe |
| 377 ± 84 | 297 ± 49 | 301 ± 90 | 328 ± 56 |
| $p < .02$ | | $p = NS$ | |

The preoperative data shows that the recalification time of the higher force-induced energy probe sample is significantly reduced when compared to the recalcification time of the lower force-induced energy probe. Surprisingly, however, there was no reduction in the postoperative values obtained with the higher force-induced energy probe when compared to the lower force-induced energy probe. Thus, the method of determining recalcification times using the variable force-induced energy input detection systems, especially probes of the present invention is able to differentiate an important aspect of clot formation undetectable by other methods. It is theorized that the additional force-induced energy imparted to the postoperative blood sample by the higher force-induced energy probe may make it more difficult to form an effective clot.

The above-described data establishes that significant differences in clotting times are obtained with the lower and higher force-induced energy input detection systems, especially probes. While these data were generated on a SONOCLOT® Analyzer, other instruments may be employed as well that provide a continuous profile, i.e., some clotting variable measured as a function of time. For example, the Thrombelastograph Coagulation Analyzer provides a continuous coagulation profile. A stationary probe remains immersed in a blood sample contained in a rotating cup. With the formation of fibrin and increasing viscosity during clotting of the blood sample, the probe no longer remains stationary, and begins to rotate. Modification of this method and device to perform in accordance with the present invention, would involve alteration of the speed at which the rotation of the cup is maintained in order to vary the input of force-induced energy to the blood sample. For example, faster rotation of the cup would add more force-induced energy to the sample through a more rapid movement of the system. This would provide the required variable force-induced energy input.

It is contemplated that many instruments currently in use or to be developed in the future, which employ a single terminal clotting time, could be modified by the artisan instructed by the description herein to obtain differential clotting times based on variable force-induced energy input to the sample. Such instruments capable of modification include, but are not limited to, those which rely on optical density reading, fibrometers, HEMOCHRONS®, HEPCONS®, and similar devices. Blood sample aliquots may be simultaneously evaluated on two or more instruments which are the same or different, and which provide a variable force-induced energy input to the aliquots, compared to each other.

The discussion herein has focused on variable force-induced energy input to a blood sample with reference to "higher" force-induced energy input and "lower" force-induced energy input. These comparative terms have been employed because a considerable range of such force-induced energy input variation is permissible, so long as it results in data which provides a basis for differentiation among patient and normal subject populations with respect to some condition or pathology. Ample guidance is provided herein with regard to the force-induced energy variation levels which are required for differentiation regarding specific conditions. With this guidance, the artisan can readily determine optimal ranges of force-induced energy input necessary to obtain adequate differentiation. It is not even necessary that only two force-induced energy levels be used, i.e., "higher" and "lower" levels, although this is preferred for obvious reasons of practicality. Intermediate levels can also be used, so long as they provide meaningful data which can differentiate normal and patient populations, and thus be used to diagnose a given existing or incipient pathology in the patients.

DESCRIPTION OF PREFERRED EMBODIMENTS

The following Examples are illustrative of the methods and devices of the present invention, and as such are not intended to be in any way a limitation of the scope of the present invention. It will be further understood by the artisan that a particular pathological state was determined to exist after a test mammal, including homo sapiens, exhibited a positive response to a method of the present invention. Further, the data with respect to healthy mammals as to a selected immunomodulator at given limits to obtain recalcification times/saline or other solvent vehicle ($RT_v$) and recalcification times/endotoxin or other modulator ($RT_i$), were used to establish a base or standard from which the mammals being tested were generally compared for ratios and differences in recalcification times/modulator ($RT_i$), thrombotic index and percent difference of clotting.

EXAMPLE 1

Clotting Assay Using Probes with Variable Force-Induced Energy Input

A 1.0 ml sample of citrated whole blood was brought up to 37° C. The sample was then gently mixed and 300 µl aliquots were pipetted into the cuvettes of two SONOCLOT® Analyzers, each cuvette containing a small magnetic stirrer. One of the SONOCLOT® Analyzers was equipped with a hollow probe, while the other was equipped with the same hollow probe sealed with bone wax supplied by ETHICON®. The samples were mixed and then the clot impedance was obtained as the magnitude of the amplitude on the y-axis.

The clot signal is the relative impedance of the sample. Values obtained for seven blood samples had the mean values ± standard deviations shown in the table of values below.

| | Hollow Probe | Hollow Probe | Bone Wax Sealed Probe | Bone Wax Sealed Probe |
|---|---|---|---|---|
| RELATIVE IMPEDANCE VALUES FOR PROBES WITH VARIABLE FORCE-INDUCED ENERGY INPUT; AND STATISTICAL SIGNIFICANCE | | | | |
| SONOCLOT® Analyzer Sensitivity | 60 (Instrument reading) | 100 (Instrument reading) | 60 (Instrument reading) | 100 (Instrument reading) |
| SONOCLOT® Analyzer Reading | 11.4 ± 1.8 | 14.7 ± 2.7 | 28.1 ± 6.0 | 45.6 ± 6.5 |
| Significance | $p < .001$ | | $p < .001$ | |

In order to determine the statistical significance of the data, the paired t-test was used with a "p" value of <0.05 being considered a showing of significance. The "r" value is the correlation coefficient; and the higher the "r" value, the better the correlation between groups. At increased sensitivity settings, both probes have greater mean values for the instrument reading of the relative impedance. However, the percent change in the hollow probe readings from the "60" to the "100" setting was only a 28.9% increase, whereas in the case of the bone wax sealed hollow probe the value increased by 62.3%, showing that the bone wax sealed hollow probe provides greater sensitivity to impedance changes than the hollow probe.

EXAMPLE 2
Recalcification Times (RT) of Hollow vs. Bone Wax Sealed Probes in Blood Samples from Emergency Room Patients Aliquots of twenty-nine (29) discarded blood samples from emergency room patients were prepared for clotting studies. In plastic vials were placed 500 ml aliquots of blood, after which they were mixed and incubated for 10 min at 37° C. From these aliquots 300 µl aliquots were pipetted into the cuvettes of two SONOCLOT® Analyzers, each cuvette containing a small magnetic stirrer and 40 µl of 0.1M calcium chloride. One of the SONOCLOT® Analyzers was equipped with a hollow probe, while the other was equipped with the same hollow probe sealed with bone wax supplied by ETHICON®. The clotting activity over time for the samples was obtained as an automatic readout on the instrument chart. The data obtained from these assays was analyzed in various ways, including variation in sensitivity of the instrument, and is set out in the table of values below.

| Mean Recalcification Times (Sec ± SD) | |
|---|---|
| Lower Force-Induced Energy Hollow Probe | Higher Force-Induced Energy Bone Wax Sealed Probe |
| 359 ± 50 | 284 ± 45 |
| Significance | $p < .0001$ |

The data in the table above show a significant reduction in the clotting times for the blood samples evaluated with the higher force-induced energy bone wax sealed probe, as compared to the clotting times obtained for the blood samples evaluated with the lower force-induced energy hollow probe. In two (2) of the twenty-nine (29) samples (6.9%), the clotting times were prolonged when evaluated with the hollow probe, as compared to the clotting times evaluated with the bone wax sealed probe. Fifteen (15) of the twenty-nine (29) patient samples (52%) had blood clotting times below 6.0 min, which is considered the lowest normal value, and thus consistent with hypercoagulability.

Figure 2:
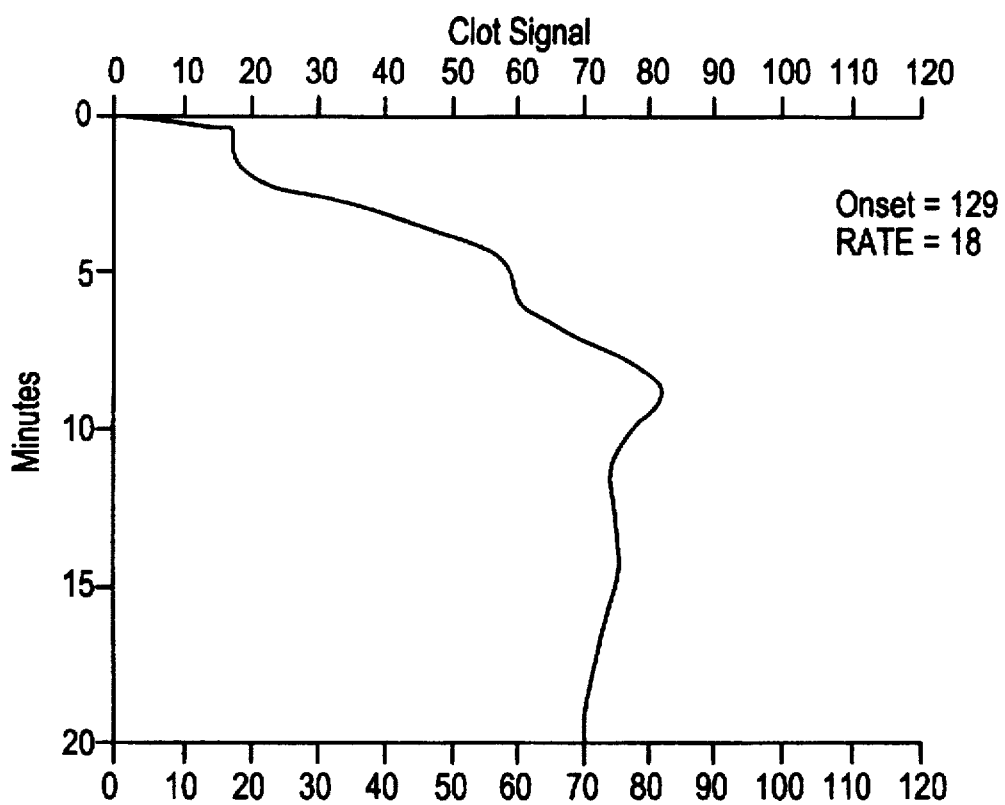
FIG. 2 depicts a coagulation profile for a whole blood sample using the lower force-induced energy input from a hollow probe.
Figure 3:
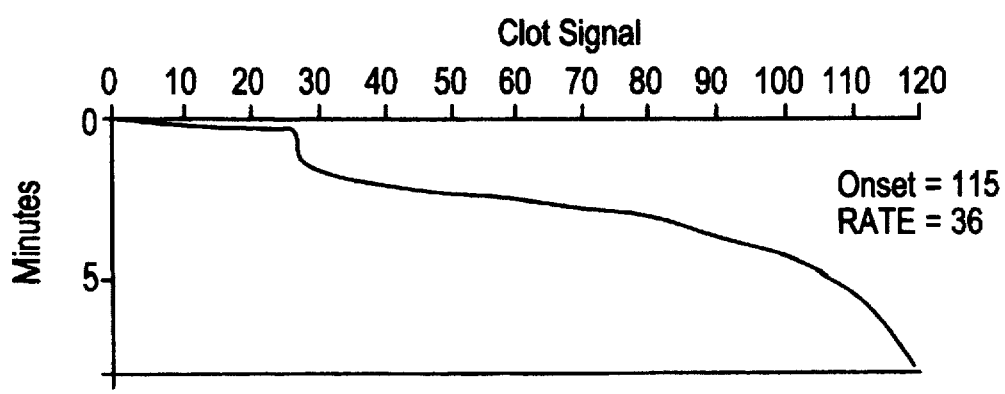
FIG. 3 depicts a coagulation profile for the same whole blood sample as in FIG. 2 using the higher force-induced energy input from a bone wax sealed probe. The bone wax filled probe has substantially altered the coagulation profile obtained as compared with that obtained by the use of the hollow probe shown in FIG. 2, resulting in elevation of relative impedance, elimination of the inflection point associated with platelet function, and increase in the maximum total impedance, a reflection of increased fibrin formation.

EXAMPLE 3
Effect of Using Probes with Different Force-Induced Energy Inputs on the Coagulation Profiles of Blood Samples Coagulation profiles were developed for whole blood samples in accordance with the procedures described above in Examples 1 and 2, using the variable force-induced energy inputs from the hollow and bone wax sealed probes. The data from these profiles established that the bone wax filled probe substantially alters the coagulation profile obtained as compared with that obtained by the use of the hollow probe, even though the same whole blood sample is involved. The bone wax sealed probe: (1) resulted in an elevation in relative impedance to 28 as compared to 17 for the hollow probe; (2) eliminated the inflection point characteristic of the coagulation profile obtained with the hollow probe, which is believed to be associated with platelet function; and (3) resulted in an increase in the maximum total impedance as compared to the result obtained with the hollow probe, which might be a reflection of increased fibrin formation. The results obtained are illustrated in FIGS. 2 and 3.

Figure 4:
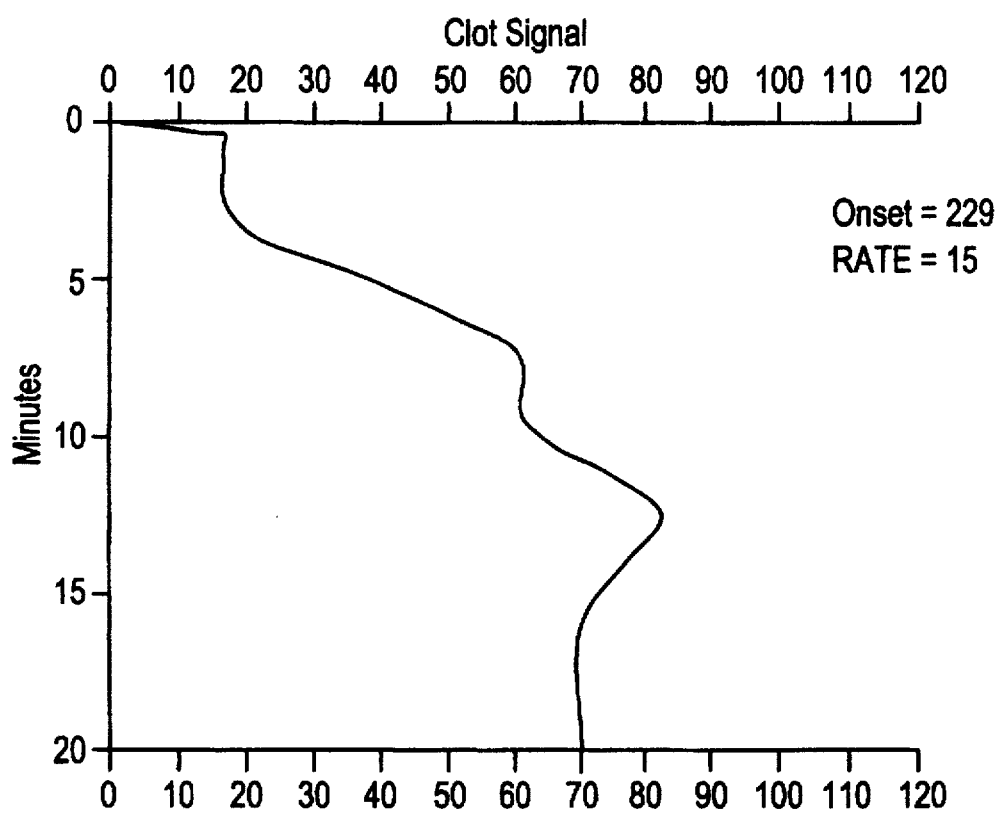
FIG. 4 depicts a coagulation profile for a whole blood sample obtained in the same manner as in FIG. 2 using the lower force-induced energy input from a hollow probe.
Figure 5:
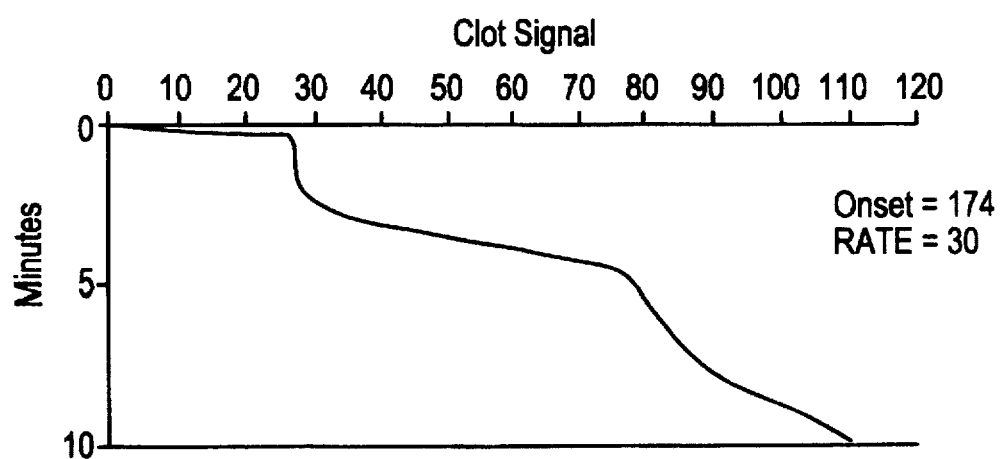
FIG. 5 depicts a coagulation profile for the same whole blood sample as in FIG. 4 obtained in the same manner as in FIG. 3, using the higher force-induced energy input from a bone wax sealed probe. The results obtained were similar to those in FIGS. 2 and 3, except that the inflection point remained present in the coagulation profile obtained using the bone wax sealed probe. Clot formation using the bone wax sealed probe, shown in FIGS. 3 and 5, took place at a significantly higher relative impedance than it did using the hollow probe, as shown in FIGS. 2 and 4.

Coagulation profiles were obtained for another set of whole blood samples in the same manner as described above, and the results obtained are illustrated in FIGS. 4 and 5. The coagulation profile obtained with the bone wax sealed probe as compared to that obtained using the hollow probe is similar to the results obtained with the previous whole blood samples described immediately above, except that the inflection point remained present in the coagulation profile obtained using the bone wax sealed probe. It is also noted for all of the whole blood samples, that clot formation using the bone wax sealed probe took place at a significantly higher relative impedance than it did using the hollow probe even though the same whole blood sample was involved, i.e., the amplitude of the clot signal was significantly greater for the bone wax sealed probe than it was for the hollow probe used on the same whole blood sample.

EXAMPLE 4
A Rapid Modulator-Induced Clotting Time Determination

It has been discovered that by using a combination of biochemical modulators, alterations in recalcification time (RT) can be induced with as little as 10 min of incubation.

To 490 µl aliquots of sixteen (16) human citrated whole blood samples is added (1) 10 µl of saline as a control; (2) 5 µl of 2.0 mg/ml soluble collagen and 5 µl saline; (3) 5 µl of 0.5 mg/ml $E.$ $coli$ endotoxin and 5 µl saline; and (4) 5 µl of collagen and 5 µl of $E.$ $coli$ endotoxin. Aliquots of these blood samples were placed in plastic vials, capped, mixed, brought to 37° C. and incubated for 10 min. Thereafter the recalcification time was determined using a dental wax sealed probe with a SONOCLOT® Coagulation Analyzer by adding 300 µl of each of the aliquots to 40 µl of 0.1M calcium chloride and recording the coagulation profile as the clotting activity over time as an automatic readout on the instrument chart. The results obtained are set out in the table of values below.

| MEAN RECALCIFICATION TIMES (min ± SD) | | | |
|---|---|---|---|
| Control | Collagen | Endotoxin | Collagen ± Endotoxin |
| 5.7 ± 1.3 | 5.2 ± 1.2 | 5.2 ± 1.2 | 4.7 ± 1.2 |
| Significance (paired 2-tailed t-test) | $p < .01$ | $p < .01$ | $p < .001$ |

In addition, the significance of the collagen or endotoxin values compared to the collagen+endotoxin value was $p<0.005$. The values obtained from this study establish that a rapid incubation time of ~10 min after the addition of one or more modulators, followed by a determination of the recalcification time or similar test, can detect a population of subjects more or less prone to alterations in clotting than a test control group of healthy individuals.

What is claimed is:

1. A method of analyzing a whole blood sample from a mammal for determination of whether or not there is a significant difference or change in values of comparative determinants of hypercoagulability in a whole blood sample of said mammal, said comparative determinants being derived from detection systems which provide variable force-induced energy inputs to said blood sample when used together with or as part of a coagulation measuring device, in order to identify the presence or incipiency of a symptomatic or asymptomatic pathology caused by or leading to said hypercoagulability, comprising:
   A. preparing anticoagulated aliquots from a whole blood sample collected from a mammal;
   B. placing a first said aliquot in a suitable container to be used as a control aliquot;
   C. placing a second said aliquot in a suitable container to be used as an active aliquot;
   D. incubating said control and said active aliquots at from about 35° C. to about 40° C. for an incubation period of up to about 1 hour or more;
   E. initiating endogenous blood coagulation altering processes in said control and said active aliquots by substantially eliminating anticoagulation;
   F. measuring a blood coagulation altering process parameter and obtaining data which are values of comparative determinants of hypercoagulability in the control and active aliquots by using two or more different detection systems or two or more different components of a single detection system which provide significantly different force-induced energy inputs to each of the control and active aliquots being measured; and
   G. identifying the presence or incipiency of a symptomatic or asymptomatic pathology caused by or leading to said hypercoagulability, by analysis of said values of the comparative determinants of hypercoagulability obtained by steps A–F for said control and active aliquots, wherein said values for each of said control and active aliquots are obtained (1) at different times from said mammal, (2) under conditions of significantly changed homeostasis of said mammal, (3) in the absence or presence of, a modulator, or (4) from the same type of mammal in a healthy state, free of said pathology, and from said mammal being tested, respectively, or any combination of (1)–(4).

2. A method according to claim 1 wherein said two or more different detection systems or said two or more different components of said single detection system which provide significantly different force-induced energy inputs to the control and active aliquots being measured, comprise two or more probes.

3. A method according to claim 2 wherein one of said two or more probes provides a significantly higher force-induced energy level input to the control and active aliquots than the other probe, when used together with a coagulation measuring device, and, wherein said probe which provides a significantly higher force-induced energy level input comprises a hollow tube of glass, ceramic, plastic or metal, an end thereof which enters said control or active aliquot to be measured, having been sealed with bone wax or dental wax.

4. A method according to claim 3 wherein said probe which provides a significantly higher force-induced energy level input comprises a hollow tube of plastic, the end thereof which enters said control or active aliquot to be measured, having been sealed with bone wax.

5. A method according to claim 2 wherein one of said two or more probes provides a significantly lower force-induced energy level input to the control and active aliquots than the other probe, when used together with a coagulation measuring device, and wherein said probe which provides a significantly lower force-induced energy level comprises a hollow tube of glass, ceramic, plastic or metal.

6. A method according to claim 1 wherein said anticoagulated aliquots are prepared by mixing said whole blood with an anticoagulating agent selected from the group consisting of sodium citrate, sodium oxalate, and EDTA.

7. A method according to claim 1 wherein said blood coagulation altering processes include blood clotting.

8. A method according to claim 1 wherein Step C. thereof additionally comprises placing a modulator together with said active aliquot in a suitable container.

9. A method according to claim 8 wherein said modulator is present in a concentration of from about 10 µg/ml to about 50 µg/ml of said active aliquot.

10. A method according to claim 8 wherein said modulator is one or more members selected from the group consisting of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities.

11. A method according to claim 10 wherein said modulator is an endotoxin or a collagen.

12. A method according to claim 8 wherein said incubation period is from about 5 minutes to about 30 minutes.

13. A method according to claim 12 wherein said incubation period is from about 10 minutes to about 15 minutes.

14. A method according to claim 8 wherein said incubation period is from about 1 to about 3 hours.

15. A method according to claim 1 wherein said incubation period is from about 5 minutes to about 30 minutes.

16. A method according to claim 15 wherein said incubation period is from about 10 minutes to about 15 minutes.

17. A method according to claim 1 wherein said incubation period is from about 1 to about 3 hours.

18. A method according to claim 1 wherein said mammal is homo sapiens.

19. A method according to claim 1 wherein said incubation of said control and active aliquots is carried out at about 37° C.

20. A method according to claim 1 wherein said blood coagulation altering process parameter data are measured and obtained at different predetermined times using two or more different probes having significantly different force-induced energy inputs to said control and active aliquots being measured, and are then compared in order to determine the presence or incipiency of said pathology in said mammal.

21. A method according to claim 20 wherein said comparison comprises:
   A. determining thrombotic index (TI) of each control and active aliquot at each predetermined time, said TI comprising a ratio of the recalcification time of said control aliquot ($RT_c$) to the recalcification time of said activate aliquot ($RT_j$), that is $TI=RT_c/RT_j$;
   B. comparing TI values for each predetermined time and each different probe with those values measured at other predetermined times and using different probes, and then further comparing said TI values with TI values for the same or substantially similar predetermined times and probes obtained by measuring whole blood samples from a same type of mammal in a healthy state, free of said pathology.

22. The method of claim 1 wherein said first aliquot is placed in said container together with a vehicle.

23. The method of claim 22 wherein said vehicle is physiological saline.

24. The method of claim 1 wherein said second aliquot is placed in said container together with a vehicle.

25. The method of claim 24 wherein said vehicle is physiological saline.

26. A method of rapidly analyzing a whole blood sample within about 0.1 to about 1.0 minute after withdrawal without the addition of anticoagulants thereto, taken from a mammal for determination of whether or not there is a significant difference or change in values of comparative determinants of hypercoagulability thereof, said values of comparative determinants being derived from detection systems which provide variable force-induced energy inputs to said blood sample when used together with or as part of a coagulation measuring device, in order to identify the presence or incipiency of a symptomatic or asymptomatic pathology caused by or leading to said hypercoagulability, comprising:
   A. withdrawing a whole blood sample from a mammal and preparing aliquots from said whole blood sample;
   B. placing a first said aliquot in a suitable container to be used as a control aliquot;
   C. placing a second said aliquot in a suitable container to be used as an active aliquot;
   D. incubating said control and active aliquots at from about 35° C. to about 40° C. for an incubation period of up to about 10 minutes, and within from about 0.1 to about 1.0 minute after said whole blood sample has been withdrawn from said mammal;
   E. permitting said control and active aliquots to undergo naturally-occurring endogenous blood coagulation altering processes;
   F. measuring a blood coagulation altering process parameter and obtaining data which are values of comparative determinants of hypercoagulability in the control and active aliquots by using two or more different detection systems or two or more different components of a single detection system which provides significantly different force-induced energy inputs to said control and said active aliquots being measured; and
   G. identifying said presence or incipiency of a symptomatic or asymptomatic pathology caused by or leading to said hypercoagulability, by analysis of said values of the comparative determinants of hypercoagulability obtained by Steps A–F for said control and active aliquots, wherein said values for each of said control and active aliquots are obtained (1) at different times from said mammal, (2) under conditions of significantly changed homeostasis of said mammal, (3) in the absence or presence of a modulator, or (4) from the same type of mammal in a healthy state, free of said pathology, and from said mammal being tested, respectively, or any combination of (1)–(4).

27. A method according to claim 26 wherein said two or more different detection systems or said two or more different components of said single detection system which provide significantly different force-induced energy inputs to the control and active aliquots being measured, comprise two or more probes.

28. A method according to claim 27 wherein one of said two or more probes provides a significantly higher force-induced energy level input to the control and active aliquots than the other probe, when used together with a coagulation measuring device, and, wherein said probe which provides a significant higher force-induced energy level input comprises a hollow tube of glass, ceramic, plastic or metal, an end thereof which enters said control or active aliquot to be measured, having been sealed with bone wax or dental wax.

29. A method according to claim 28 wherein said probe which provides a significantly higher force-induced energy level input comprises a hollow tube of plastic, the end thereof which enters said control or active aliquot to be measured, having been sealed with bone wax.

30. A method according to claim 27 wherein one of said two or more probes provides a significantly lower force-induced energy level input to the control and active aliquots than the other probe, when used together with a coagulation measuring device, and wherein said probe which provides a significantly lower force-induced energy level input comprises a hollow tube of glass, ceramic, plastic or metal.

31. A method according to claim 26 wherein said incubation of said control and said active aliquots takes place at about 37° C.

32. A method according to claim 26 wherein said incubation period is up to about 5 minutes.

33. A method according to claim 32 wherein said incubation period is in the range of from about 1 minute to about 4 minutes.

34. A method according to claim 33 wherein said incubation period is from about 1.5 minutes to about 3 minutes.

35. A method according to claim 26 wherein Step C. thereof additionally comprises placing a modulator together with said active aliquot in a suitable container.

36. A method according to claim 35 wherein said modulator is present in a concentration of from about 10 µg/ml to about 50 µg/ml of said active aliquot.

37. A method according to claim 35 wherein said modulator comprises one or more members selected from the group consisting of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities.

38. A method according to claim 39 wherein said modulator is an endotoxin or a collagen.

39. A method according to claim 35 wherein said incubation of said control and said active aliquots takes place at about 37° C.

40. A method according to claim 35 wherein said incubation period is up to about 5 minutes.

41. A method according to claim 40 wherein said incubation period is in the range of from about 1 minute to about 4 minutes.

42. A method according to claim 41 wherein said incubation period is from about 1.5 minutes to about 3 minutes.

43. A method according to claim 26 wherein said mammal is homo sapiens.

44. A method according to claim 26 wherein said blood coagulation altering process parameter data are measured and obtained at different predetermined times using two or more different probes having significantly different force-induced energy inputs to said control and active aliquots being measured, and are then compared in order to determine the presence or incipiency of said pathology in said mammal.

45. A method according to claim 44 wherein said comparison comprises:
   A. determining a thrombotic index (TI) of each control and active aliquot at each predetermined time, said TI comprising a ratio of the recalcification time of said control aliquot ($RT_v$) to the recalcification time of said activate aliquot ($RT_i$), that is $TI=RT_v/RT_i$;
   and B. comparing TI values for each predetermined time and each different probe with those values measured at other predetermined times and using different probes, and then further comparing said TI values with TI values for the same or substantially similar predetermined times and probes obtained by measuring whole blood samples from a same type of mammal in a healthy state, free of said pathology.

46. The method of claim 26 wherein said first aliquot is placed in said container together with a vehicle.

47. The method of claim 46 wherein said vehicle is physiological saline.

48. The method of claim 26 wherein said second aliquot is placed in said container together with a vehicle.

49. The method of claim 48 wherein said vehicle is physiological saline.

50. A prepackaged diagnostic kit for use together with a coagulation measuring device for analyzing a whole blood sample to be taken from a mammal for determination of whether or not there is a significant difference or change in the values of comparative determinants of hypercoagulability thereof, said comparative determinants being derived from detection systems which provide variable force-induced energy inputs to said blood sample when used together with or as part of a coagulation measuring device, in order to identify the presence or incipiency of a symptomatic or asymptomatic pathology caused by or leading to said hypercoagulability, comprising:
   A. at least one first container and at least one second container suitable for receiving aliquots of a whole blood sample from a mammal to serve as control and active aliquots, respectively, for determination of blood coagulation altering process parameters thereof when used together with a coagulation measuring device, and for obtaining data which are values of comparative determinants of hypercoagulability for said control and active aliquots;
   B. at least two third containers containing means for initiating endogenous blood coagulation altering processes in said control and said active aliquots by substantially eliminating anticoagulation thereof, wherein said third containers are suitable for subsequent measurement of said blood coagulation altering process parameter and obtaining data which are values of comparative determinants of hypercoagulability;
   C. two or more different detection systems or two or more different components of a single detection system capable of providing significantly different force-induced energy inputs to said control and active aliquots being measured; and
   D. a diagnostic protocol for determination of a pathology by analysis of said values of the comparative determinants of hypercoagulability obtained by measurement of a blood coagulation altering process parameter in said control and active aliquots using said two or more different detection systems or two or more different components of a single detection system which provide significantly different force-induced energy inputs to each of the control and active aliquots, wherein said values for each of said control and active aliquots are obtained (1) at different times from said mammal, (2) under conditions of significantly changed homeostasis of said mammal, (3) in the absence or presence of a modulator, or (4) from the same type of mammal in a healthy state, free of the presence or incipiency of said pathology, and from said mammal being tested, respectively, or any combination of (1)–(4).

51. A prepackaged diagnostic kit according to claim 50 wherein said two or more different detection systems or said two or more different components of said single detection system which provide significantly different force-induced energy inputs to the control and active aliquots being measured, comprise two or more probes.

52. A prepackaged diagnostic kit according to claim 51 wherein one of said two or more probes provides a significantly higher force-induced energy level input to the control and active aliquots being tested than the other probe, when used together with a coagulation measuring device, and, wherein said probe which provides a significantly higher force-induced energy level input comprises a hollow tube of glass, ceramic, plastic or metal, an end thereof which enters said control and active aliquot to be measured, having been sealed with bone wax or dental wax.

53. A prepackaged diagnostic kit according to claim 52 wherein said probe which provides a significantly higher force-induced energy level input comprises a hollow tube of plastic, the end thereof which enters said control or active aliquot to be measured, having been sealed with bone wax.

54. A prepackaged diagnostic kit according to claim 51 wherein one of said two or more probes provides a significantly lower force-induced energy level input to the control and active aliquots being tested than the other probe, when used together with a coagulation measuring device, and wherein said probe which provides a significantly lower force-induced energy level input comprises a hollow tube of glass, ceramic, plastic or metal.

55. A prepackaged diagnostic kit according to claim 51 wherein at least one of said probes has coated thereon a predetermined amount of a preselected modulator before being introduced into said control or active aliquot to be measured.

56. A prepackaged diagnostic kit according to claim 55 wherein said predetermined amount of said preselected modulator has previously been coated on said at least one probe.

57. A prepackaged diagnostic kit according to claim 55 wherein said predetermined amount of said preselected modulator is provided in a separate container from which it is then applied to and coated on said at least one probe.

58. A prepackaged diagnostic kit according to claim 50 wherein said at least one second container is for preparing an active aliquot and wherein said kit may additionally have present in said at least one second container for preparing said active aliquot, a predetermined amount of a preselected modulator.

59. A prepackaged diagnostic kit according to claim 50 wherein:

said at least one first container and said at least one second container each has a predetermined amount of a preselected anticoagulating agent therein for preparing one or more anticoagulated aliquots of said whole blood sample to serve as control and active aliquots.

60. A prepackaged diagnostic kit according to claim 59 wherein said anticoagulating agent in said at least one first and second containers is selected from the group consisting of sodium citrate, sodium oxalate, and ethylenediamine tetraacetic acid (EDTA).

61. A prepackaged diagnostic kit according to claim 59 wherein said at least one first or second containers additionally comprise a predetermined amount of a preselected modulator for use together with said control or active aliquots.

62. A prepackaged diagnostic kit according to claim 61 wherein said modulator in said at least one or second container is present in a concentration of from about 10 μg/ml to about 50 μg/ml of anticoagulated whole blood.

63. A prepackaged diagnostic kit according to claim 61 wherein said modulator comprises one or more members selected from the group consisting of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities.

64. A prepackaged diagnostic kit according to claim 63 wherein said modulator is an endotoxin or a collagen.

65. A prepackaged diagnostic kit according to claim 50 wherein there is additionally provided in said kit a heating means for obtaining and maintaining an incubation temperature of about 37° C.

66. The kit of claim 50 wherein said at least one first container contains a vehicle.

67. The kit of claim 66 wherein said vehicle is physiological saline.

68. The kit of claim 50 wherein said at least one second container contains a vehicle.

69. The kit of claim 68 wherein said vehicle is physiological saline.

70. The kit of claim 50 additionally comprising a fourth container, wherein said fourth container contains a vehicle for dispensing to said first container, said second container, or to both said first and second containers.

71. The kit of claim 70 wherein said vehicle is physiological saline.

72. Probes for use together with a coagulation measuring device for analyzing a whole blood sample to be taken from a mammal for determination of whether or not there is a significant difference or change in values of comparative determinants of hypercoagulability thereof, said comparative determinants being derived from detection systems which provide variable force-induced energy inputs to said blood sample when used together with or as a part of a coagulation measuring device, in order to identify the presence or incipiency of a symptomatic or asymptomatic pathology caused by or leading to said hypercoagulability, comprising at least one first and second probe wherein:

A. said at least one first probe provides a significantly higher force-induced energy level input to samples being tested than said at least one second probe, when used together with a coagulation measuring device, which comprises a hollow tube of glass, ceramic, plastic or metal, an end thereof which enters a sample to be measured, having been sealed with bone wax or dental wax; and B. said at least one second probe provides a significantly lower force-induced energy level input to samples being tested than said of least one first probe, when used together with a coagulation measuring device, which comprises of a hollow tube of glass, ceramic, plastic or metal.

73. Probes according to claim 72 wherein said at least one first probe which provides a significantly higher force-induced energy level input comprises a hollow tube of plastic, the end thereof which enters said sample to be measured, having been sealed with bone wax.

74. Probes at least one first and second according to claim 72 wherein each of said probes additionally has coated thereon a predetermined amount of a preselected modulator before being introduced into said sample to be measured.

75. Probes according to claim 74 wherein each of said at least one first and second probes has been coated with a preselected modulator which is a blood cell coagulation activator or inhibitor.

76. Probes according to claim 74 wherein said predetermined amount of said preselected modulator is provided in a separate container from which it is then applied to and coated on each of said at least one first and second probe.

* * * * *